United States Patent
Sun et al.

(10) Patent No.: US 11,214,654 B2
(45) Date of Patent: Jan. 4, 2022

(54) NANOCOMPOSITE HYDROGEL, AND PREPARATION METHOD AND USE THEREOF

(71) Applicant: Qingdao Agricultural University, Qingdao (CN)

(72) Inventors: Qingjie Sun, Qingdao (CN); Liu Xiong, Qingdao (CN); Shengju Ge, Qingdao (CN); Hao Lu, Quindao (CN); Man Li, Quindao (CN); Mei Zhao, Qingdao (CN)

(73) Assignee: Qingdao Agricultural University, Qingdao (CN)

( * ) Notice: Subject to any disclaimer, the term of this patent is extended or adjusted under 35 U.S.C. 154(b) by 114 days.

(21) Appl. No.: 16/183,937

(22) Filed: Nov. 8, 2018

(65) Prior Publication Data
US 2019/0135989 A1    May 9, 2019

(30) Foreign Application Priority Data

Nov. 8, 2017  (CN) .......................... 201711092597.7

(51) Int. Cl.

| | | |
|---|---|---|
| C08J 3/075 | (2006.01) | |
| C08B 30/12 | (2006.01) | |
| C08B 30/20 | (2006.01) | |
| C08J 9/00 | (2006.01) | |
| C12P 19/16 | (2006.01) | |
| C08L 89/06 | (2006.01) | |
| C08L 3/12 | (2006.01) | |

(52) U.S. Cl.
CPC ............... *C08J 3/075* (2013.01); *C08B 30/12* (2013.01); *C08B 30/20* (2013.01); *C08J 9/0061* (2013.01); *C08L 3/12* (2013.01); *C08L 89/06* (2013.01); *C12P 19/16* (2013.01); *C08J 2205/022* (2013.01); *C08J 2205/06* (2013.01); *C08J 2207/10* (2013.01); *C08J 2303/12* (2013.01); *C08J 2389/00* (2013.01); *C08J 2389/06* (2013.01); *C08J 2403/12* (2013.01); *C08J 2489/06* (2013.01)

(58) Field of Classification Search
CPC . C08L 3/12; C08L 89/06; C08B 30/12; C08B 30/20; C08J 2201/048; C08J 2205/022; C08J 2205/06; C08J 2207/00; C08J 2207/10; C08J 2303/12; C08J 2389/00; C08J 2389/06; C08J 2403/12; C08J 2489/06; C08J 3/075; C08J 9/0061; C08J 9/28; C12P 19/14; C12P 19/16
See application file for complete search history.

(56) References Cited

PUBLICATIONS

"Viscoelasticity of gelatinized starch dispersions", by I.D. Evans and A. Lips, Journal of Texture Studies, published Mar. 1992, vol. 23, Issue 1. (Year: 1992).*

* cited by examiner

*Primary Examiner* — Audrea B Coniglio (57) ABSTRACT

The present invention provides a nanocomposite hydrogel and a preparation method thereof, and relates to the field of nanocomposite materials. The nanocomposite hydrogel is prepared by mixing completely gelatinized short amylose with an aqueous gelatin solution having a mass concentration of 8%-14%, and then cooling. The present invention utilizes the nanoparticles formed by in-situ self-assembly of the short amylose in the aqueous gelatin solution as a reinforcing agent, and the nanoparticles are uniformly distributed in the hydrogel to form a stable crystallization system, such that the prepared nanocomposite hydrogel exhibits optimal mechanical properties in terms of viscoelasticity, hardness, compressive stress, etc. The preparation process of the present invention is green and environmentally friendly, simple and efficient, and can be widely applied to the fields of food, cosmetics and medicine.

8 Claims, 7 Drawing Sheets

FIG. 7

NANOCOMPOSITE HYDROGEL, AND PREPARATION METHOD AND USE THEREOF

CROSS-REFERENCE TO RELATED APPLICATIONS

This application claims priority to Chinese application number 201711092597.7, filed 8 Nov. 2017, with a title of NANOCOMPOSITE HYDROGEL AND PREPARATION METHOD AND USE THEREOF. The above-mentioned patent application is incorporated herein by reference in its entirety.

FIELD OF INVENTION

The present invention relates to the field of hydrogels, and in particular to a nanocomposite hydrogel and a preparation method and use thereof.

BACKGROUND OF RELATED ART

A natural hydrogel is a three-dimensional biopolymer network that is capable of absorbing and maintaining large amounts of water and has potential application values in food, cosmetics and biomedical fields due to its biodegradability, biocompatibility and renewability.

It is required that the hydrogel has a high strength and flexibility as well as reversible deformation characteristics when applied. However, a common chemically-crosslinked polymer hydrogel is fragile under certain pressure. The following methods have attempted to enhance the mechanical properties of the hydrogel, including a crosslinked hydrogel, a dual network hydrogel, and a nanocomposite hydrogel. Among these methods, the nanocomposite hydrogel preparation method is simple and thus has attracted much attention.

Simply mixing a nanoparticle with a hydrogel to enhance the mechanical properties of the hydrogel has been investigated. However, since the nanoparticle of a high concentration is not easily dispersed uniformly in the hydrogel, the mechanical properties of the nanocomposite hydrogel are not well improved.

Gelatin is a fibrin that is obtained by partially degrading collagen contained in an animal connective tissue. A gelatin hydrogel is widely used in the food industry such as desserts, jellies, and the like due to the biocompatibility and biodegradability of gelatin. However, gelatin has limited application due to its poor mechanical properties.

SUMMARY OF THE INVENTION

An objective of the present invention is to provide a nanocomposite hydrogel having optimal mechanical properties and a preparation method thereof.

The present invention provides a method for preparing a nanocomposite hydrogel, including the following steps:

(1) gelatinizing short amylose; and (2) mixing the gelatinized short amylose with an aqueous gelatin solution having a mass concentration of 8%-14%, and then cooling to obtain the nanocomposite hydrogel.

Preferably, the amount of the short amylose added into the aqueous gelatin solution is 0.01-0.1 g/ml.

Preferably, the mixing temperature is 40-60° C.

Preferably, the cooling temperature is 4-14° C., and the cooling time is 10-24 h.

Preferably, the method for preparing the short amylose comprises the following steps:
  i. mixing a waxy corn starch solution with a disodium hydrogen phosphate-citric acid buffer solution, and gelatinizing in a boiling water bath to obtain a gelatinized product;
  ii. mixing the gelatinized product with pullulanase according to an enzyme dosage of 3-5 u/g, and conducting eenzymatic degradation at 50-60° C. for 6-10 h;
  iii. conducting enzyme deactivation on the enzymoiysis product obtained in step ii; and
  iv. mixing the liquid material obtained after enzyme deactivation in step iii with 2-6 volumes of absolute ethanol to obtain a solid precipitate, separating the solid precipitate, and conducting freeze-drying to obtain the short amylose.

Preferably, in step i, the waxy corn starch solution has a mass concentration of 1-30%.

Preferably, in step i, after the disodium hydrogen phosphate-citric acid buffer solution is mixed with the waxy corn starch solution, the pH of the mixed solution is 4-5.

Preferably, in step iv, the freeze-drying temperature is −90° C. to −80° C.; and the time is 36-72 h.

The present invention provides a nanocomposite hydrogel prepared by the above preparation method, where, the particle size of nanoparticles of the nanocomposite hydrogel is 200-600 nm; the nanocomposite hydrogel has a reduced pore size as compared with that of a pure gelatin hydrogel; the storage modulus and the loss modulus are respectively increased by 300-1,000 Pa and 10-70 Pa, the hardness is increased by 10-90 g, and the fracture stress is increased by 0.03-0.015 MPa. The nanocomposite hydrogel added with 5% short linear gelatin has a compressive stress increased by 2-3 times as compared with the pure gelatin hydrogel.

The present invention also provides the use of the nanocomposite hydrogel prepared by the above preparation method in food, medicine or cosmetics.

BENEFICIAL EFFECTS

The present invention provides a nanocomposite hydrogel and a preparation method thereof. The nanocomposite hydrogel is prepared by mixing gelatinized short amylose with an aqueous gelatin solution having a mass concentration of 8%-14%, and then cooling.

The gelatinized short amylose can form a nanoparticle in situ by self-assembly, and the nanoparticle formed by self-assembly of the short amylose has a small particle size, is uniformly distributed, and can interact with a gelatin matrix in such a manner that the prepared nanocomposite hydrogel exhibits optimal mechanical properties in terms of viscoelasticity, hardness, compressive stress, and the like. Moreover, the preparation method provided by the present invention is simple, efficient, green and environmentally friendly, and can be widely applied to the fields of food, cosmetics and medicine.

In the present invention, a waxy corn starch is selected, then subjected to gelatinization, enzymatic degradation, enzyme deactivation and precipitation in absolute ethanol, and freeze-dried to obtain the short amylose. The short amylose has a simple preparation method, abundant sources, a low price, and relatively greater biocompatibility.

DETAILED DESCRIPTION

The present invention provides a method for preparing a nanocomposite hydrogel, including the following steps:
(1) gelatinizing short amylose; and
(2) mixing the gelatinized short amylose with an aqueous gelatin solution having a mass concentration of 8%-14%, and then cooling to obtain the nanocomposite hydrogel.

The present invention has no particular limitation on the source of the short amylose, and the short amylose may be conventionally commercially available or self-made. If the short amylose is self-made, the method for preparing the short amylose preferably includes the following steps:
i. mixing a waxy corn starch solution with a disodium hydrogen phosphate-citric acid buffer solution, and gelatinizing in a boiling water bath to obtain a gelatinized product;
ii. mixing the gelatinized product with pullulanase according to an enzyme dosage of 3-5 u/g, and conducting eenzymatic degradation at 50-60° C. for 6-10 h;
iii. conducting enzyme deactivation on the enzymoiysis product obtained in step ii; and
iv. mixing the liquid material obtained after enzyme deactivation in step iii with 2-6 volumes of absolute ethanol to obtain a solid precipitate, separating the solid precipitate, and conducting freeze-drying to obtain the short amylose.

In the present invention, the mass concentration of the waxy corn starch solution in step i is preferably 1-30%, and more preferably 10%; the pH of the disodium hydrogen phosphate-citric acid buffer solution is 4-5, and more preferably 4.6; and the mixing ratio of the disodium hydrogen phosphate-citric acid buffer solution and the waxy corn starch is 8-15:1, and preferably 10:1.

The resultant mixed solution is gelatinized. In the present invention, the gelatinization time is preferably 20-40 min, and more preferably 30 min. Under the gelatinization conditions, the waxy corn starch can be stably gelatinized, such that the molecules in the starch granules are extended and diffused in all directions.

The gelatinized product is subjected to enzymatic degradation. In the present invention, the enzyme used for the enzymatic degradation is pullulanase with the enzyme dosage of 3-5 u/g, and preferably 4 u/g. The enzymatic degradation temperature is 50-60° C., and preferably 58° C.; and the enzymatic degradation time is 6-10 h, and preferably 8 h.

The enzymoiysis product is subjected to enzyme deactivation to obtain an enzymoiysis solution after the enzyme deactivation. The present invention has no particular limitation on the enzyme deactivation manner of step iii, and the enzyme deactivation manner is preferably enzyme deactivation by boiling water bath. For enzyme deactivation by boiling water bath, the enzyme deactivation time is preferably 10-20 min, and more preferably 15 min. With the enzyme deactivation time, not only it can be ensured that the enzyme activity is lost, but also it can avoid the structure of the short amylose from being destroyed.

The enzymoiysis solution after the enzyme deactivation is mixed with absolute ethanol to obtain a solid precipitate. The solid precipitate is then separated and freeze-dried to obtain the short amylose. In the present invention, the absolute ethanol is added in an amount of 4-6 times, and preferably 5 times the volume of the enzymoiysis solution. Under the operation, the short amylose can be precipitated and separated in large amounts from water. The freeze-drying temperature is preferably −90° C. to −80° C., and more preferably −86° C.; and the freeze-drying time is preferably 36-72 h. The moisture content in the short amylose is 7% after the freeze-drying, and the short amylose is obtained after freeze-drying.

After the short amylose is prepared, it is necessary to gelatinize the short amylose. The present invention has no particular limitation on the gelatinization conditions of the short amylose, and the requirements for preparing the nanocomposite hydrogel can be satisfied as long as the short amylose can be gelatinized. Preferably, at the time of the gelatinization, the temperature is 150° C. and the time is 10 min.

The gelatinized short amylose is mixed with an aqueous gelatin solution having a mass concentration of 8%-14%, and then cooled to obtain the nanocomposite hydrogel.

In the present invention, the aqueous gelatin solution has a mass concentration of 8%-14%, preferably 9-12%, and more preferably 10%. The aqueous gelatin solution provides a self-assembled environment for the short amylose; and meanwhile it also provides a gel structure for the nanocomposite hydrogel. The present invention has no particular limitation on the source of the gelatin, and the gelatin may be commercially available conventionally.

In the present invention, after the gelatinized short amylose and the aqueous gelatin solution are obtained, the gelatinized short amylose is mixed with the aqueous gelatin solution having a mass concentration of 8%-14%.

The present invention has no particular limitation on the mixing order. For example, the gelatinized short amylose may be added into the aqueous gelatin solution, or the aqueous gelatin solution may be poured into the gelatinized short amylose. In the present invention, the amount of the short amylose added into the aqueous gelatin solution is preferably 0.01-0.1 g/ml, more preferably 0.03-0.08 g/ml, and further 0.05 g/ml (i.e., 5.0% w/v). The short amylose can form nanoparticles by self-assembly to enhance the mechanical properties of the nanocomposite hydrogel.

In the present invention, the gelatinized short amylose is mixed with the aqueous gelatin solution having a mass concentration of 8%-14%. The temperature of the mixed solution is preferably 40-60° C., and more preferably 45° C. With the mixing temperature, the short amylose can be gradually self-assembled in situ in the aqueous gelatin solution to form an interconnected nanoparticle network structure; and the aqueous gelatin solution can be in a stable and completely dissolved state.

In the present invention, after the mixed solution is obtained through mixing, the mixed solution is cooled to obtain an in-situ self-assembled nanocomposite hydrogel. In the present invention, the cooling temperature is preferably 4-14° C., and more preferably 10° C. The cooling time is 10-24 h, and preferably 12 h. The purpose of cooling is to promote the coagulation of gelatin and the self-assembly of the short amylose. With the cooling temperature and the cooling time, the nanocomposite hydrogel is obtained. The formed nano starch hydrogel has strong viscoelasticity, hardness and compressive stress.

Figure 1:
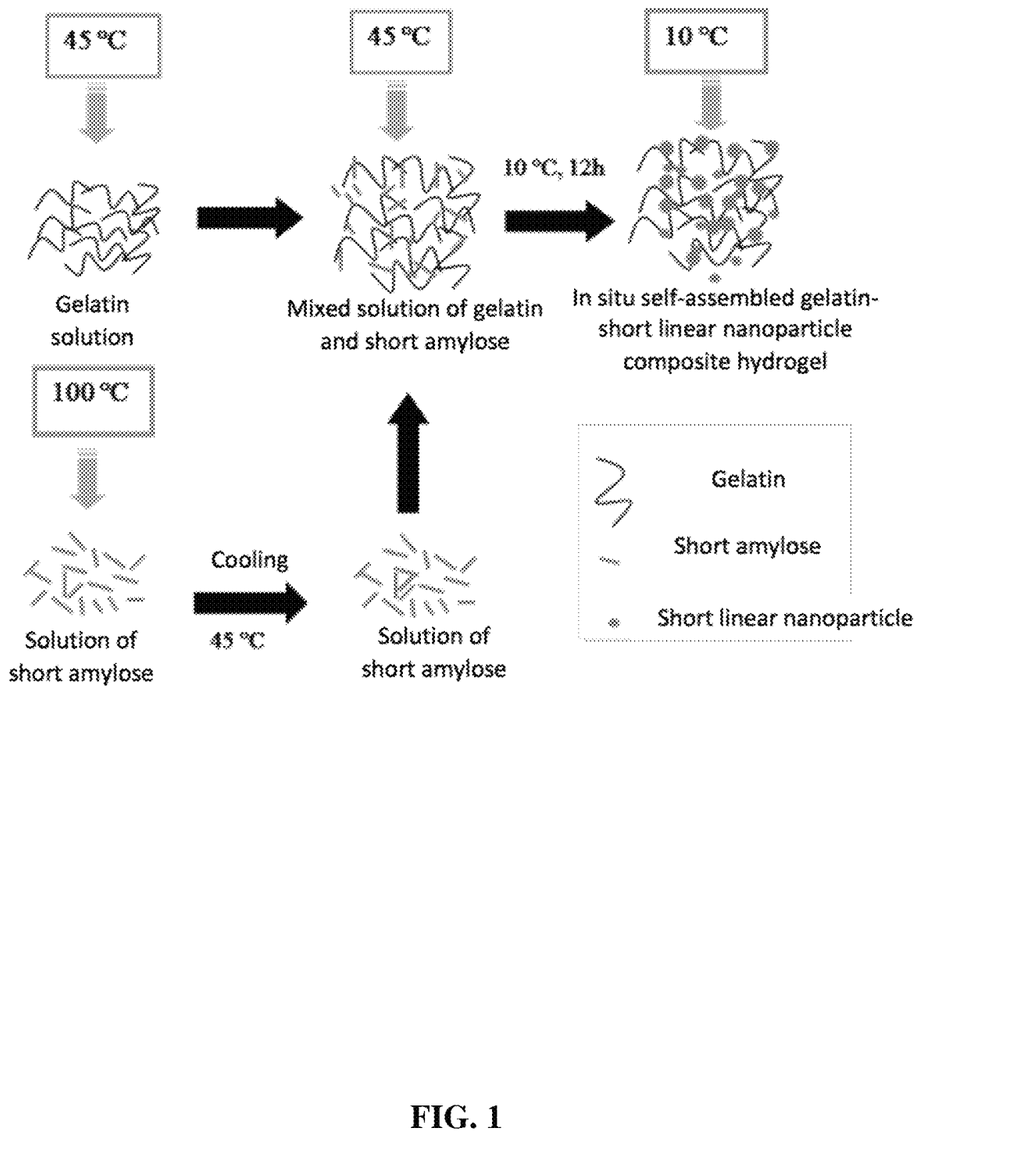
FIG. 1 is a preparation flowchart of the nanocomposite hydrogel according to embodiments of the present invention.
Figure 2:
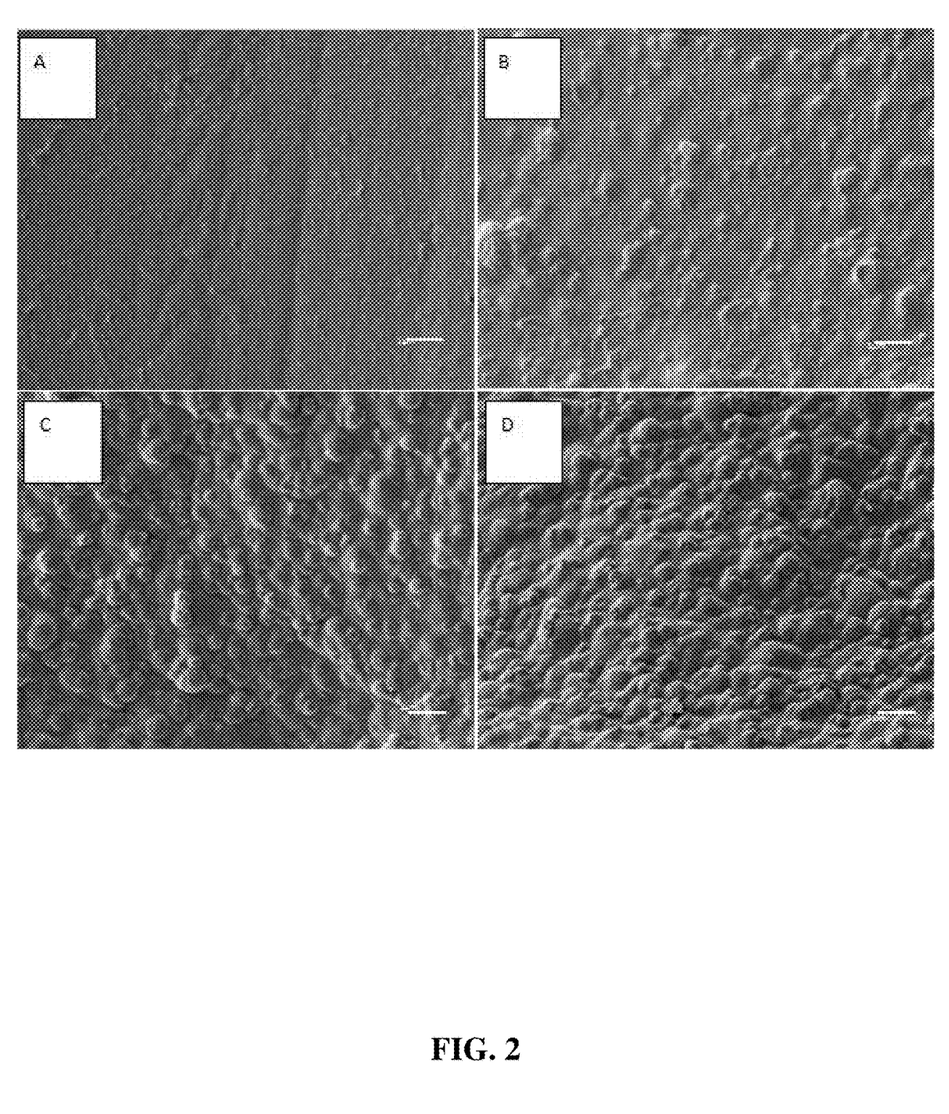
FIG. 2 is a surface scanning graph of a gelatin hydrogel and the nanocomposite hydrogel of the present invention; where A: 10% gelatin; B: 10% gelatin+1% short amylose; C: 10% gelatin+3% short amylose; and D: 10% gelatin+5% short amylose.
Figure 3:
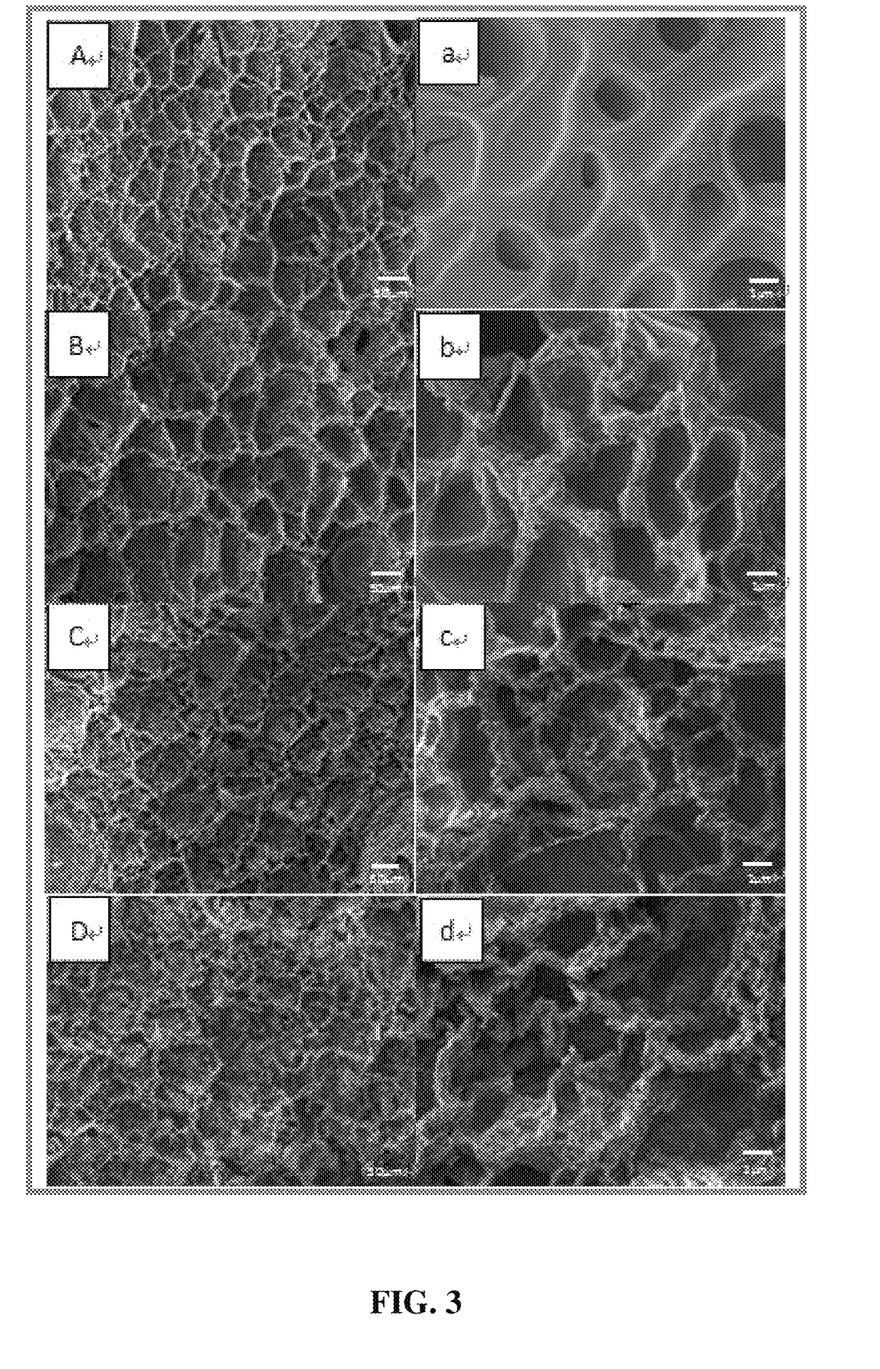
FIG. 3 is a section scanning graph of a gelatin hydrogel and the nanocomposite hydrogel of the present invention; where A: 10% gelatin; B: 10% gelatin+1% short amylose; C: 10% gelatin+3% short amylose; and D: 10% gelatin+5% short amylose; and a, b, c, and d are respectively enlarged views of A, B, C and D.

FIGS. 2-3 show that, spherical particles of 200-600 nm appear on the surface of the nanocomposite hydrogel, and as the adding amount of the short amylose increases, the number of the spherical particles increases, indicating that the short amylose is self-assembled to form nanoparticles in the gelatin matrix during cooling. It can be seen from the sectional view that the nanocomposite hydrogel has a porous microstructure, indicating that the original network structure can be maintained after the in situ process, and the particle size of the nanoparticles decreases and the number of the nanoparticles increases along with the increase of the short amylose content.

Figure 4:
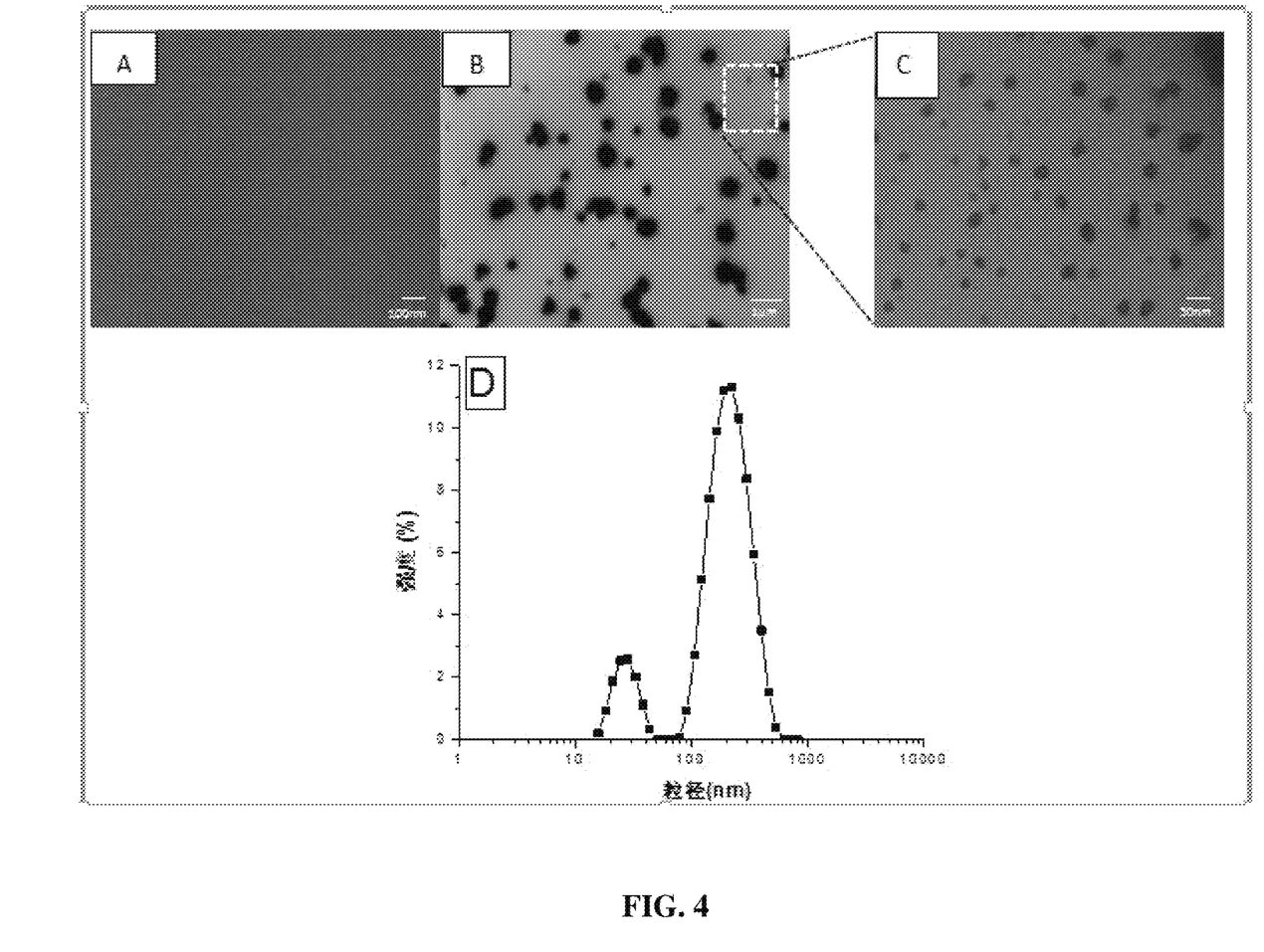
FIG. 4 is a transmission diagram and particle size distribution diagram of gelatin and nanoparticles formed by self-assembly of the short amylose of the present invention; where A: a transmission diagram of gelatin; B: a transmission diagram of the nanoparticles formed by self-assembly of the short amylose; C is an enlarged view of B; and D is a particle size distribution diagram of the nanoparticles formed by self-assembly of the short amylose.

FIG. 4 illustrates that, the nanoparticles separated from the composite hydrogel have a particle size of 200-600 nm, particles having a smaller particle size are also present, and the particle size is also confirmed by the particle size distribution diagram. This also demonstrates that the short amylose is self-assembled to form nanoparticles in the gelatin matrix.

Figure 5:
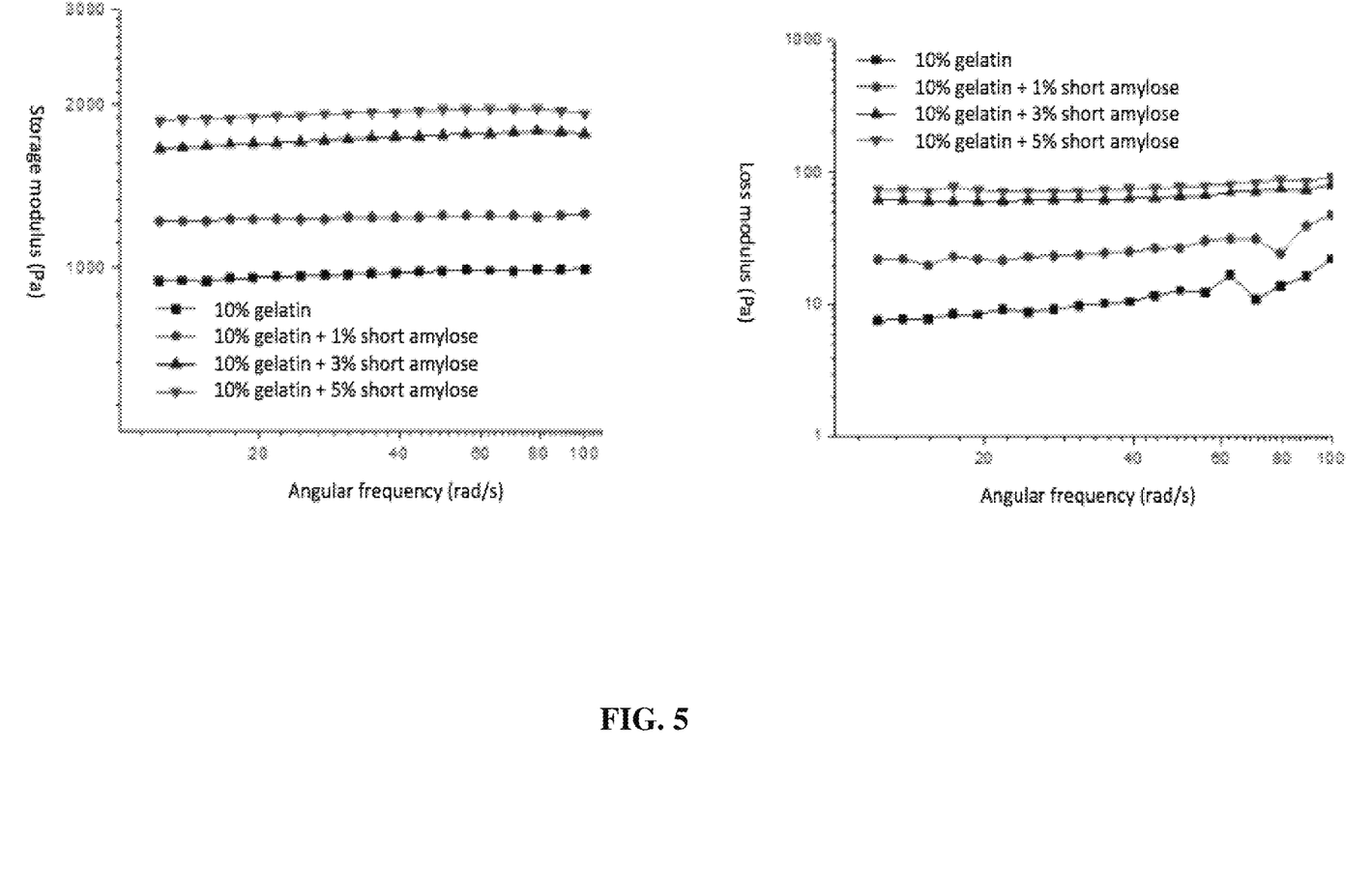
FIG. 5 is an infrared spectrogram of the nanocomposite hydrogel of the present invention.

FIG. 5 illustrates that the nanocomposite hydrogel formed in-situ has viscoelasticity which is significantly improved than that of the gelatin hydrogel, and when the adding amount of the short amylose is 5%, the storage modulus of the nanocomposite hydrogel is 2 times larger than that of the gelatin gel. It is indicated that gelatin forms a stable composite matrix with the short linear nanoparticles.

Figure 6:
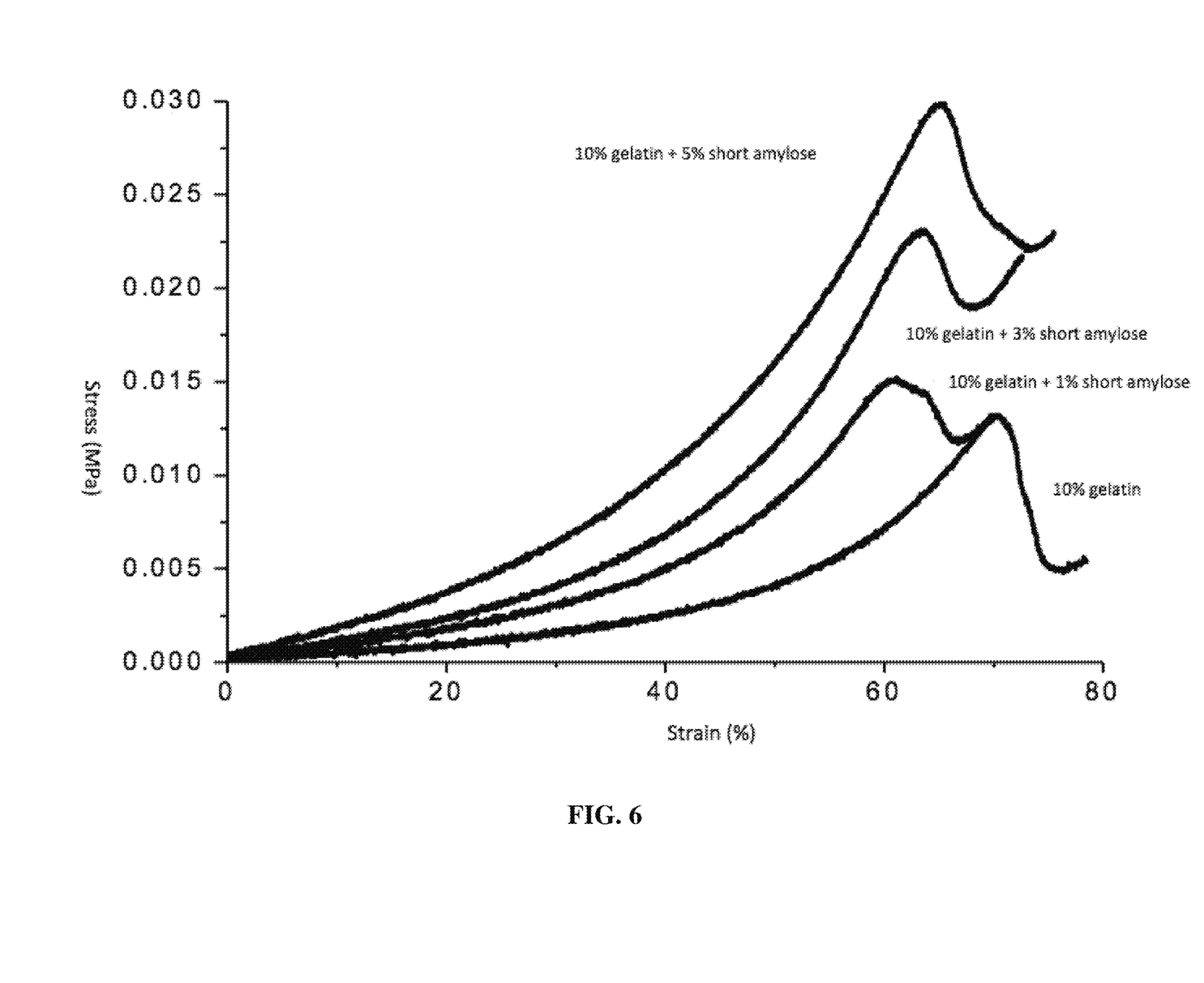
FIG. 6 is a frequency scanning graph of the nanocomposite hydrogel of the present invention.

FIG. 6 illustrates that, the compressive stress of the nanocomposite hydrogel gradually increases along with the increase in the concentration of the short amylose, and when the adding amount of the short amylose is 5%, the compressive stress of the nanocomposite hydrogel is 3 times larger than that of the gelatin hydrogel. It is indicated that the short linear nanoparticle composite hydrogel formed in gelatin has relatively stronger mechanical properties.

Figure 7:
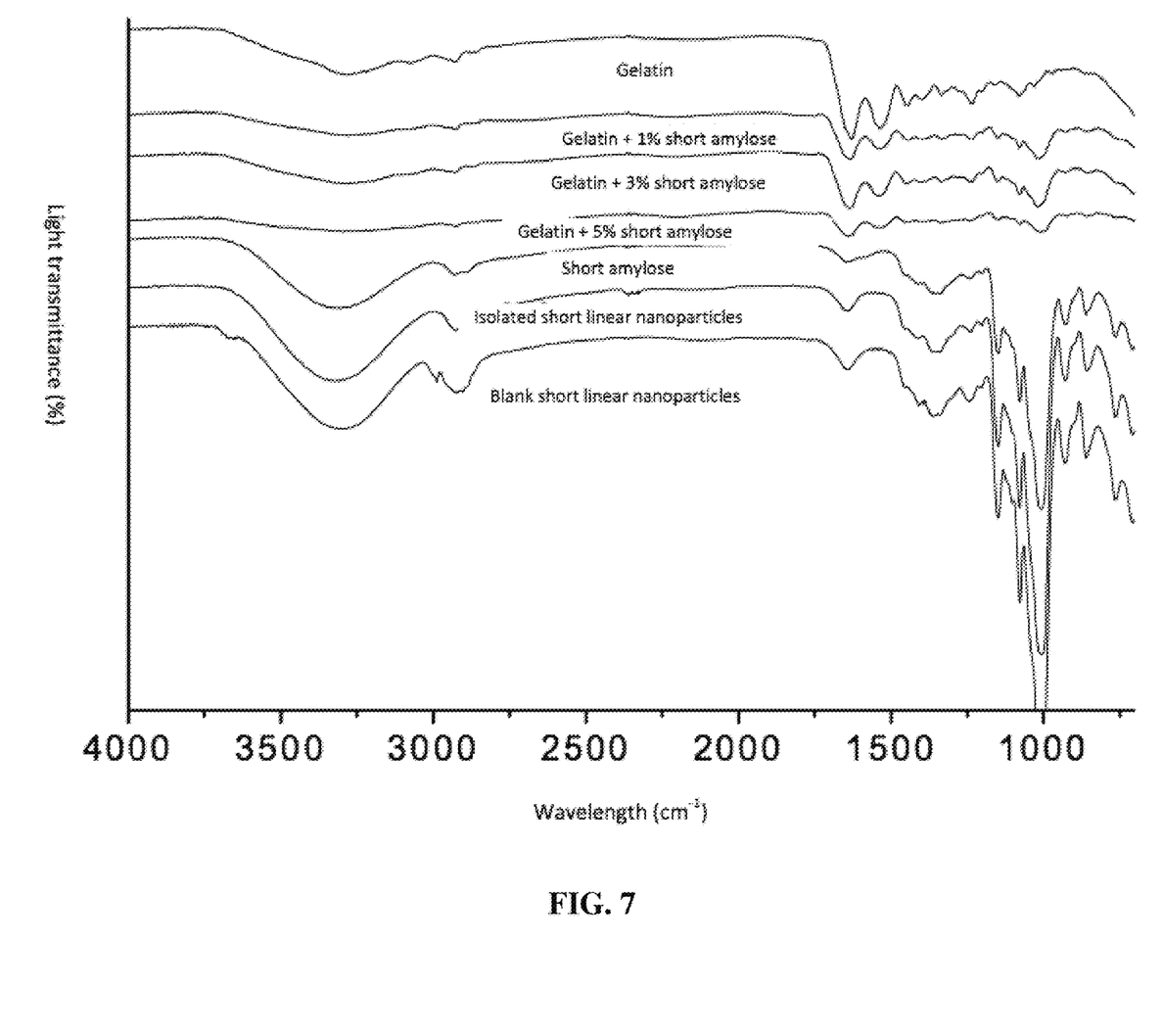
FIG. 7 is a strain curve showing the compressive stress of the nanocomposite hydrogel of the present invention.

FIG. 7 illustrates that, the amide A bond in gelatin moves towards to a low frequency along with the increase in concentration of the short amylose, indicating a hydrogen bond interaction between the short linear nanoparticles in gelatin and the gelatin molecule.

The present invention provides a nanocomposite hydrogel prepared by the above preparation method. The nanoparticles of the nanocomposite hydrogel have a particle size of 200-600 nm; the corresponding pressure is 0.014-0.025 MPa when the nanocomposite hydrogel generates a 60% strain; the nanocomposite hydrogel has a reduced pore size as compared with that of a pure gelatin hydrogel; the storage modulus and the loss modulus are respectively increased by 300-1,000 Pa and 10-70 Pa, the hardness is increased by 10-90 g, and the fracture stress is increased by 0.03-0.015 MPa. The nanocomposite hydrogel added with 5% short linear gelatin has a compressive stress increased by 2-3 times as compared with the pure gelatin hydrogel.

The nanocomposite hydrogel exhibits optimal mechanical properties in terms of viscoelasticity, hardness, compressive stress, etc., and details are as shown in Table 1:

TABLE 1

Texture characteristics of the nanocomposite hydrogel

| Short Amylose (% w/v) | Hardness (g force) | Elasticity | Cohesion | Viscosity (g force) | Chewiness (g force) | Restoring force |
|---|---|---|---|---|---|---|
| 0 | 77.336 ± 2.14$^c$ | 1.030 ± 0.022$^a$ | 0.880 ± 0.012$^a$ | 68.090 ± 1.74$^d$ | 70.162 ± 2.74$^d$ | 0.628 ± 0.031$^b$ |
| 1 | 90.635 ± 3.76$^c$ | 0.940 ± 0.019$^a$ | 0.929 ± 0.018$^a$ | 84.197 ± 3.01$^c$ | 79.181 ± 2.15$^c$ | 0.727 ± 0.012$^a$ |
| 3 | 135.896 ± 2.27$^b$ | 0.948 ± 0.008$^a$ | 0.824 ± 0.009$^b$ | 111.923 ± 2.77$^b$ | 106.134 ± 3.21$^b$ | 0.645 ± 0.024$^{ab}$ |
| 5 | 168.529 ± 5.96$^a$ | 0.939 ± 0.013$^a$ | 0.790 ± 0.014$^b$ | 133.148 ± 4.33$^a$ | 125.017 ± 3.57$^a$ | 0.576 ± 0.012$^b$ |

Note:
the numbers in the table are mean ± standard deviation (n = 3), and the letters in the same column indicate significant differences ($p < 0.05$).

Table 1 shows that, compared with the gelatin hydrogel, the short linear nanoparticle composite hydrogel has a hardness significantly increased along with the increase in the concentration of the short amylose, and when the adding amount of the short amylose is 5%, the nanocomposite hydrogel has a hardness which is 2 times larger than that of the gelatin hydroge, and the viscosity and chewiness of the nanocomposite hydrogel are also significantly increased.

The present invention also provides use of the nanocomposite hydrogel prepared by the above preparation method in food, medicine or cosmetics: the nanocomposite hydrogel prepared by the above preparation method is used as a carrier, and is combined with other nutritional ingredients, medicinal active ingredients or cosmetic ingredients to make an end product. The dosage of the nanocomposite hydrogel when applied is preferably that, when the adding amount of the short amylose is 5%, the concentration of gelatin is 10%.

The nanocomposite hydrogel, and the preparation method and use thereof as provided by the present invention will be described in detail in connection with the following embodiments, but they should not be construed as limiting the claimed scope of the present invention.

Embodiment 1

A method for preparing a short amylose includes the following steps:
i. weighing 6 g waxy corn starch, adding 100 ml of a disodium hydrogen phosphate-citric acid buffer solution and distilled water into the waxy corn starch to prepare a starch solution with a concentration of 6%;

ii. adjusting the pH of the starch solution to 4.6 with the disodium hydrogen phosphate-citric acid buffer solution, and then water-bath heating under a condition of boiling water bath for 30 min;

iii. adding pullulanase and reacting for 8 h under water bath at a constant temperature of 58° C.;

iv. conducting enzyme deactivation under a boiling water bath for 15 min; and v. adding 4 volumes of absolute ethanol, centrifuging with a centrifugal machine to remove the supernatant and obtain a solid precipitate; then washing with water for 2-3 times, and conducting freeze-drying in a freeze-drying machine, where the freeze-drying conditional parameters were: a temperature of −86° C., a pressure of 20 Pa, and a time of 48 h; and obtaining the short amylose after the freeze-drying.

A method for preparing a nanocomposite hydrogel includes the following steps:

A. formulating an aqueous gelatin solution with a mass concentration of 10%, which was ready for use;

B. completely gelatinizing the short amylose at a condition of 100° C., cooling down to 45° C., and then the gelatinized short amylose was ready for use;

C. mixing the short amylose at the gelatinized state with the aqueous gelatin solution under a condition of 45° C.; where the amount of the short amylose added into the aqueous gelatin solution is 0.05 g/ml; and D. cooling at a condition of 10° C. for 12 h, to prepare a gelatin-short linear nanoparticle composite hydrogel self-assembled in situ.

Embodiment 2

A method for preparing a short amylose includes the following steps:

i. weighing 6 g waxy corn starch, adding 100 ml of a disodium hydrogen phosphate-citric acid buffer solution and distilled water into the waxy corn starch to prepare a starch solution with a concentration of 6%;

ii. adjusting the pH of the starch solution to 4.6 with the disodium hydrogen phosphate-citric acid buffer solution, and then water-bath heating under a condition of boiling water bath for 30 min;

iii. adding pullulanase and reacting for 8 h under water bath at a constant temperature of 58° C.;

iv. conducting enzyme deactivation under a boiling water bath for 15 min; and v. adding 4 volumes of absolute ethanol, centrifuging with a centrifugal machine to remove the supernatant and obtain a solid precipitate; then washing with water for 2-3 times, and conducting freeze-drying in a freeze-drying machine, where the freeze-drying conditional parameters were: a temperature of −86° C., a pressure of 20 Pa, and a time of 48 h; and obtaining the short amylose after the freeze-drying.

A method for preparing a nanocomposite hydrogel includes the following steps:

A. formulating an aqueous gelatin solution with a mass concentration of 10%, which was ready for use;

B. completely gelatinizing the short amylose at a condition of 100° C., cooling down to 45° C., and then the gelatinized short amylose was ready for use;

C. mixing the short amylose at the gelatinized state with the aqueous gelatin solution under a condition of 45° C.; where the amount of the short amylose added into the aqueous gelatin solution is 0.01 g/ml; and D. cooling at a condition of 10° C. for 12 h, to prepare a gelatin-short linear nanoparticle composite hydrogel self-assembled in situ.

Embodiment 3

A method for preparing a short amylose includes the following steps:

i. weighing 6 g waxy corn starch, adding 100 ml of a disodium hydrogen phosphate-citric acid buffer solution and distilled water into the waxy corn starch to prepare a starch solution with a concentration of 6%;

ii. adjusting the pH of the starch solution to 4.6 with the disodium hydrogen phosphate-citric acid buffer solution, and then water-bath heating under a condition of boiling water bath for 30 min;

iii. adding pullulanase and reacting for 8 h under water bath at a constant temperature of 58° C.;

iv. conducting enzyme deactivation under a boiling water bath for 15 min; and v. adding 4 volumes of absolute ethanol, centrifuging with a centrifugal machine to remove the supernatant and obtain a solid precipitate; then washing with water for 2-3 times, and conducting freeze-drying in a freeze-drying machine, where the freeze-drying conditional parameters were: a temperature of −86° C., a pressure of 20 Pa, and a time of 48 h; and obtaining the short amylose after the freeze-drying.

A method for preparing a nanocomposite hydrogel includes the following steps:

A. formulating an aqueous gelatin solution with a mass concentration of 10%, which was ready for use;

B. completely gelatinizing the short amylose at a condition of 100° C., cooling down to 45° C., and then the gelatinized short amylose was ready for use;

C. mixing the short amylose at the gelatinized state with the aqueous gelatin solution under a condition of 45° C.; where the amount of the short amylose added into the aqueous gelatin solution is 0.03 g/ml; and D. cooling at a condition of 10° C. for 12 h, to prepare a gelatin-short linear nanoparticle composite hydrogel self-assembled in situ.

Embodiment 4

A method for preparing a short amylose includes the following steps:

i. weighing 20 g waxy corn starch, adding 100 ml of a disodium hydrogen phosphate-citric acid buffer solution and distilled water into the waxy corn starch to prepare a starch solution with a concentration of 20%;

ii. adjusting the pH of the starch solution to 4.6 with the disodium hydrogen phosphate-citric acid buffer solution, and then water-bath heating under a condition of boiling water bath for 40 min;

iii. adding pullulanase and reacting for 8 h under water bath at a constant temperature of 59° C.;

iv. conducting enzyme deactivation under a boiling water bath for 20 min; and v. adding 4 volumes of absolute ethanol, centrifuging with a centrifugal machine to remove the supernatant and obtain a solid precipitate; then washing with water for 2-3 times, and conducting freeze-drying in a freeze-drying machine, where the freeze-drying conditional parameters were: a temperature of −86° C., a pressure of 20 Pa, and a time of 48 h; and obtaining the short amylose after the freeze-drying.

A method for preparing a nanocomposite hydrogel includes the following steps:
A. formulating an aqueous gelatin solution with a mass concentration of 10%, which was ready for use;
B. completely gelatinizing the short amylose at a condition of 100° C., cooling down to 45° C., and then the gelatinized short amylose was ready for use;
C. mixing the short amylose at the gelatinized state with the aqueous gelatin solution under a condition of 45° C.; where the amount of the short amylose added into the aqueous gelatin solution is 0.1 g/ml; and
D. cooling at a condition of 10° C. for 12 h, to prepare a gelatin-short linear nanoparticle composite hydrogel self-assembled in situ.

Embodiment 5

A method for preparing a short amylose includes the following steps:
i. weighing 15 g waxy corn starch, adding 100 ml of a disodium hydrogen phosphate-citric acid buffer solution and distilled water into the waxy corn starch to prepare a starch solution with a concentration of 15%;
ii. adjusting the pH of the starch solution to 4.6 with the disodium hydrogen phosphate-citric acid buffer solution, and then water-bath heating under a condition of boiling water bath for 25 min;
iii. adding pullulanase and reacting for 7 h under water bath at a constant temperature of 58° C.;
iv. conducting enzyme deactivation under a boiling water bath for 18 min; and
v. adding 6 volumes of absolute ethanol, centrifuging with a centrifugal machine to remove the supernatant and obtain a solid precipitate; then washing with water for 2-3 times, and conducting freeze-drying in a freeze-drying machine, where the freeze-drying conditional parameters were: a temperature of −80° C., a pressure of 300 Pa, and a time of 50 h; and obtaining the short amylose after the freeze-drying.

A method for preparing a nanocomposite hydrogel includes the following steps:
A. formulating an aqueous gelatin solution with a mass concentration of 8%, which was ready for use;
B. completely gelatinizing the short amylose at a condition of 80° C., cooling down to 40° C., and then the gelatinized short amylose was ready for use;
C. mixing the short amylose at the gelatinized state with the aqueous gelatin solution under a condition of 40° C.; where the amount of the short amylose added into the aqueous gelatin solution is 0.05 g/ml; and
D. cooling at a condition of 4° C. for 12 h, to prepare a gelatin-short linear nanoparticle composite hydrogel self-assembled in situ.

Embodiment 6

A method for preparing a short amylose includes the following steps:
i. weighing 10 g waxy corn starch, adding 100 ml of a disodium hydrogen phosphate-citric acid buffer solution and distilled water into the waxy corn starch to prepare a starch solution with a concentration of 10%;
ii. adjusting the pH of the starch solution to 4.6 with the disodium hydrogen phosphate-citric acid buffer solution, and then water-bath heating under a condition of boiling water bath for 35 min;
iii. adding pullulanase and reacting for 9 h under water bath at a constant temperature of 59° C.;
iv. conducting enzyme deactivation under a boiling water bath for 20 min; and
v. adding 5 volumes of absolute ethanol, centrifuging with a centrifugal machine to remove the supernatant and obtain a solid precipitate; then washing with water for 2-3 times, and conducting freeze-drying in a freeze-drying machine, where the freeze-drying conditional parameters were: a temperature of −90° C., a pressure of 15 Pa, and a time of 40 h; and obtaining the short amylose after the freeze-drying.

A method for preparing a nanocomposite hydrogel includes the following steps:
A. formulating an aqueous gelatin solution with a mass concentration of 14%, which was ready for use;
B. completely gelatinizing the short amylose at a condition of 100° C., cooling down to 60° C., and then the gelatinized short amylose was ready for use;
C. mixing the short amylose at the gelatinized state with the aqueous gelatin solution under a condition of 60° C.; where the amount of the short amylose added into the aqueous gelatin solution is 0.05 g/ml; and
D. cooling at a condition of 14° C. for 24 h, to prepare a gelatin-short linear nanoparticle composite hydrogel self-assembled in situ.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

We claim:

1. A method for preparing a nanocomposite hydrogel, comprising the following steps:
(1) gelatinizing amylose, wherein the method for preparing the amylose comprises the following steps:
   i.) mixing a waxy corn starch solution with a disodium hydrogen phosphate-citric acid buffer solution, and gelatinizing in a boiling water bath to obtain a gelatinized product;
   ii.) mixing the gelatinized product with pullulanase according to an enzyme dosage of 3-5 u/g, and conducting enzymatic degradation at 50-60° C. for 6-10 h;
   iii.) conducting enzyme deactivation on the enzymolysis product obtained in step ii; and
   iv.) mixing the liquid material obtained after enzyme deactivation in step iii with 2-6 volumes of absolute ethanol to obtain a solid precipitate, separating the solid precipitate, and conducting freeze-drying to obtain the amylose; and
(2) mixing the gelatinized amylose with an aqueous gelatin solution having a mass concentration of 8%-14%, and then cooling to obtain the nanocomposite hydrogel, wherein the amount of the amylose added into the aqueous gelatin solution is 0.01-0.1 g/ml, the mixing temperature is 40-60° C., the cooling temperature is 4-14° C., and the cooling time is 10-24 h.

2. The method for preparing the nanocomposite hydrogel according to claim 1, wherein in step i, the waxy corn starch solution has a mass concentration of 1-30%.

3. The method for preparing the nanocomposite hydrogel according to claim 1, wherein in step i, after the disodium hydrogen phosphate-citric acid buffer solution is mixed with the waxy corn starch solution, the pH of the mixed solution is 4-5.

4. The method for preparing the nanocomposite hydrogel according to claim 1, wherein in step iv, the freeze-drying temperature is −90° C. to −80° C.; and the time is 36-72 h.

5. A nanocomposite hydrogel prepared by the method according to claim 1, wherein the nanoparticles in the nanocomposite hydrogel have a particle diameter of 200-600 nm.

6. A nanocomposite hydrogel prepared by the method according to claim 2, wherein the nanoparticles in the nanocomposite hydrogel have a particle diameter of 200-600 nm.

7. A nanocomposite hydrogel prepared by the method according to claim 3, wherein the nanoparticles in the nanocomposite hydrogel have a particle diameter of 200-600 nm.

8. A nanocomposite hydrogel prepared by the method according to claim 4, wherein the nanoparticles in the nanocomposite hydrogel have a particle diameter of 200-600 nm.

* * * * *

UNITED STATES PATENT AND TRADEMARK OFFICE
CERTIFICATE OF CORRECTION

| | | |
|---|---|---|
| PATENT NO. | : 11,214,654 B2 | Page 1 of 1 |
| APPLICATION NO. | : 16/183937 | |
| DATED | : January 4, 2022 | |
| INVENTOR(S) | : Qingjie Sun et al. | |

It is certified that error appears in the above-identified patent and that said Letters Patent is hereby corrected as shown below:

On the Title Page

At item (72) Inventors:, for the two instances of the inventors' city name "Quindao", each occurrence should read --Qingdao--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*